(12) United States Patent
Kirk et al.

(10) Patent No.: US 9,359,234 B2
(45) Date of Patent: Jun. 7, 2016

(54) METHODS AND SYSTEMS FOR TREATING AN AQUEOUS EFFLUENT

(71) Applicant: Elevance Renewable Sciences, Inc., Woodridge, IL (US)

(72) Inventors: Sharon Kirk, Woodridge, IL (US); Brian Pease, Woodridge, IL (US); Bruce Firth, Woodridge, IL (US); Bradon Dreyer, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 37 days.

(21) Appl. No.: 14/601,443

(22) Filed: Jan. 21, 2015

(65) Prior Publication Data

US 2015/0210568 A1 Jul. 30, 2015

Related U.S. Application Data

(60) Provisional application No. 61/933,642, filed on Jan. 30, 2014.

(51) Int. Cl.
*C02F 1/72* (2006.01)
*C02F 101/30* (2006.01)
*C02F 103/36* (2006.01)

(52) U.S. Cl.
CPC ............... *C02F 1/725* (2013.01); *C02F 1/722* (2013.01); *C02F 2101/30* (2013.01); *C02F 2103/36* (2013.01); *C02F 2305/02* (2013.01)

(58) Field of Classification Search
CPC ............ C02F 1/72; C02F 1/722; C02F 1/725; C02F 1/727; C02F 1/74; C02F 1/76; C02F 1/78; C02F 2101/30; C02F 2103/36; C02F 2305/02

See application file for complete search history.

(56) References Cited

U.S. PATENT DOCUMENTS

| 2008/0103346 | A1* | 5/2008 | Burdett | B01D 61/027 585/818 |
| 2011/0113679 | A1* | 5/2011 | Cohen | C10G 45/00 44/388 |
| 2011/0160472 | A1* | 6/2011 | Lemke | C10G 3/47 554/154 |
| 2011/0313180 | A1* | 12/2011 | Uptain | C10G 3/47 554/124 |
| 2013/0085288 | A1 | 4/2013 | Snead et al. | |
| 2013/0331586 | A1 | 12/2013 | Dreyer et al. | |

FOREIGN PATENT DOCUMENTS

| EP | 0281311 | 9/1988 |
| WO | 2011/124587 | 10/2011 |

OTHER PUBLICATIONS

International Search Report, PCT App. No. PCT/US2015/012148, dated Apr. 30, 2015.

* cited by examiner

*Primary Examiner* — Lucas Stelling
(74) *Attorney, Agent, or Firm* — Robert S. Dailey

(57) ABSTRACT

Methods and systems for treating an aqueous effluent from a metathesis reactor, such as a metathesis-based biorefinery, are generally disclosed. In some embodiments, the aqueous effluent is generated from washing the metathesized product with an aqueous medium. In some embodiments, such wash streams are chemically treated to reduce their toxicity and to facilitate disposal. In some embodiments, such wash streams are treated to recover at least a portion of the catalyst residue, so as to facilitate catalyst recovery.

20 Claims, 6 Drawing Sheets

200

201 Providing polar medium including metathesis catalyst residues and an organic phosphine and/or organic phosphonium compound 202 Reacting the organic phosphine and/or organic phosphonium compound to for an organic phosphine oxide compound

METHODS AND SYSTEMS FOR TREATING AN AQUEOUS EFFLUENT

CROSS-REFERENCE TO RELATED APPLICATIONS

The present application claims the benefit of priority to U.S. Provisional Application No. 61/933,642, filed Jan. 30, 2014, which is hereby incorporated by reference as though fully set forth herein.

TECHNICAL FIELD

Methods and systems for treating an aqueous effluent from a metathesis reactor, such as a metathesis-based biorefinery, are generally disclosed. In some embodiments, the aqueous effluent is generated from washing the metathesized product with an aqueous medium. In some embodiments, such wash streams are chemically treated to reduce their toxicity and to facilitate disposal. In some embodiments, such wash streams are treated to recover at least a portion of the catalyst residue, so as to facilitate catalyst recovery.

BACKGROUND

Olefin metathesis provides a powerful tool for transforming certain natural oil compounds or their derivatives into higher-value chemical compounds, such as 9-decenoic acid and esters thereof. Such processes can include reacting a natural oil or its derivative in the presence of a metathesis catalyst.

In some instances, the process involves homogeneous catalysis, which makes it difficult to recover the used catalyst by simple filtering. Catalyst loss can therefore detract from the economic viability of the metathesis process, especially if the catalyst is expensive or in short supply. Therefore, it can be desirable to develop means of recovering at least a portion of the used catalyst from the reaction products and thereby enhance the economic viability of the process. In some instances, the used catalyst is at least partially soluble in aqueous media, and may therefore be separated from the metathesized product by contacting the metathesized product composition with a wash solution.

The wash solution may also capture other water-soluble species in the metathesized product composition. For example, aldehydes, such as formaldehyde, can be present in the metathesized product composition, and pass into the wash solution when the metathesized product is subjected to an aqueous wash. Further, in some instances, certain phosphonium salts can be present in the metathesized product composition, which also pass into the wash solution during washing. These phosphonium salts can be generated as part of the catalyst deactivation process.

Species such as formaldehyde and phosphonium salts may cause environmental harm. Thus, their presence in a wash solution may limit disposal options and therefore increase the cost of the process. It can therefore be desirable to develop methods of chemically treating the wash stream to convert these species to more innocuous species, and thereby widen the potential disposal options.

Thus, there is a continuing need to develop methods of treating metathesis biorefinery wash streams, so as to recover catalyst and/or reduce the toxicity of certain species that may be present in such wash streams.

SUMMARY

In a first aspect, the disclosure provides methods of treating a reactor water stream, the method comprising: providing a first aqueous medium comprising (i) an organic phosphine compound or an organic phosphonium compound, and (ii) a metathesis catalyst residue; and reacting the organic phosphine compound or the organic phosphonium compound with an oxidizing agent to form a second aqueous medium comprising an organic phosphine oxide.

In a second aspect, the disclosure provides methods of refining a natural-oil-derived feedstock, comprising: providing a feedstock comprising a natural oil or a derivative thereof; reacting the feedstock in the presence of a metathesis catalyst to form a metathesized product that comprises unsaturated esters and olefins; introducing an organic phosphine compound or an organic phosphonium compound to the metathesized product; washing the metathesized product with an aqueous wash solution to generate a washed metathesized product and a first aqueous medium comprising (i) an organic phosphine compound or an organic phosphonium compound, and (ii) a metathesis catalyst residue; separating at least a portion of the first aqueous medium from the washed metathesized product; and treating the separated first aqueous medium according to the method of any embodiments of the first aspect.

Further aspects and embodiments are provided in the foregoing drawings, detailed description, and claims.

BRIEF DESCRIPTION OF THE DRAWINGS

The following drawings are provided to illustrate certain embodiments described herein. The drawings are merely illustrative, and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
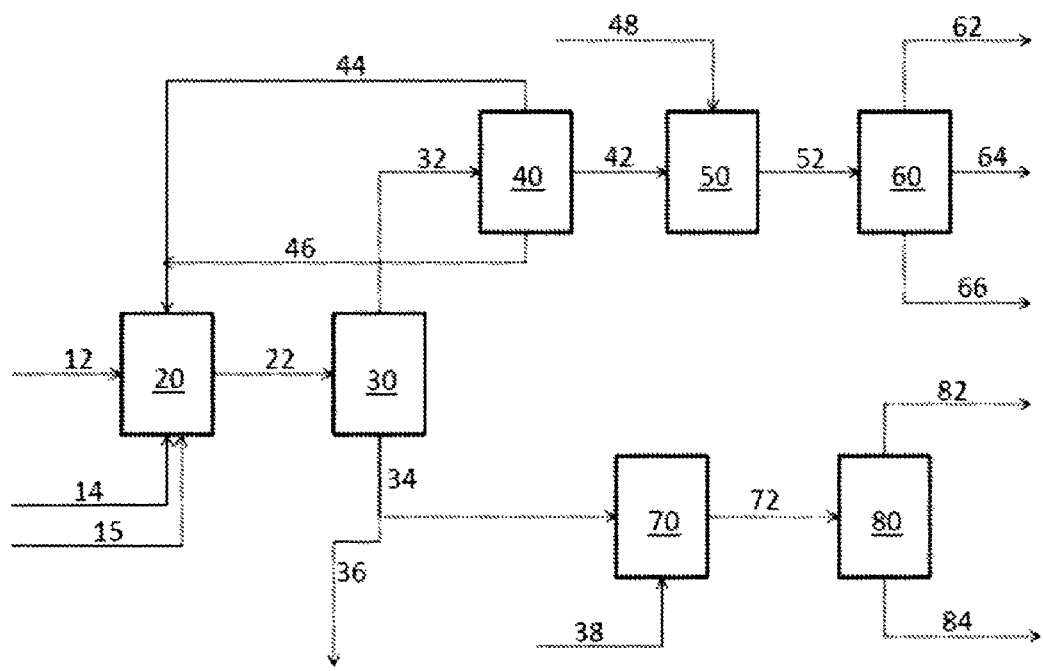
FIG. 1 shows an illustrative embodiment for incorporating olefin metathesis into a biorefinery.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

DEFINITIONS

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, "metathesis catalyst" refers to any catalyst or catalyst system that catalyzes an olefin metathesis reaction.

As used herein, "metathesis catalyst residue" refers to any compound or system of compounds derived from a metathesis catalyst. For example, in some embodiments where the metathesis catalyst is a ruthenium alkylidene complex, the metathesis catalyst residue can refer to the ruthenium compounds that are generated following the use of the metathesis catalyst to catalyze an olefin metathesis reaction. In some embodiments, the metathesis catalyst residue can include metathesis catalyst resides that are further derivatized, for example, to inactivate the compounds (and thereby prevent them from catalyzing undesirable reactions, such as isomerization reactions). In some other embodiments, the term can refer to analogous molybdenum- or tungsten-based complexes, which can also be used as metathesis catalysts.

As used herein, "catalyst recovery" refers broadly to the process of separating at least a portion of a metathesis catalyst, a metathesis catalyst residue, or a derivative thereof, from a post-reaction stream, e.g., for purposes of reclaiming the metal (e.g., ruthenium, osmium, tungsten, molybdenum, etc.) and using it to make new catalyst compounds.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "passivate" or "passivation," with reference to a metathesis catalyst or a metathesis catalyst residue, refers to treatment (e.g., chemical treatment) of the catalyst or catalyst residue to reduce the degree to which the catalyst or catalyst residue catalyzes reactions involving carbon-carbon double bonds.

As used herein, "peroxide decomposition catalyst" refers to any catalyst that catalyzed the decomposition of peroxides, including inorganic and/or organic peroxides.

As used herein, "hydrocarbon" refers to an organic group composed of carbon and hydrogen, which can be saturated or unsaturated, and can include aromatic groups. The term "hydrocarbyl" refers to a monovalent or polyvalent hydrocarbon moiety.

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin," while an olefin having a non-terminal carbon-carbon double bond can be referred to as an "internal olefin."

As used herein, the term "low-molecular-weight olefin" may refer to any one or combination of unsaturated straight, branched, or cyclic hydrocarbons in the $C_{2-14}$ range. Low-molecular-weight olefins include "alpha-olefins" or "terminal olefins," wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-6}$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. In one embodiment, it may be preferable to use a mixture of linear and branched $C_4$ olefins (i.e., combinations of: 1-butene, 2-butene, and/or isobutene). In other embodiments, a higher range of $C_{11-C14}$ may be used.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "poly-unsaturated alkene" refers to an alkene having two or more carbon-carbon double bonds. A "lower alkene," as used herein, refers to an alkene having from 2 to 10 carbon atoms.

As used herein, "alpha-olefin" refers to an olefin (as defined above) that has a terminal carbon-carbon double bond. In some embodiments, the alpha-olefin is a terminal alkene, which is an alkene (as defined above) having a terminal carbon-carbon double bond. Additional carbon-carbon double bonds can be present.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified.

It is noted that an olefin may also comprise an ester, and an ester may also comprise an olefin, if the R or R' group in the general formula R—COO—R' contains an unsaturated carbon-carbon double bond. Such compounds can be referred to as "unsaturated esters" or "olefin esters." Further, a "terminal olefin ester" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "carboxylic acid" or "carboxylic acids" refer to compounds having the general formula: R—COOH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "carboxylic acids" may refer to a group of compounds with the general formula described above, wherein the compounds have different carbon lengths. The term "carboxyl" refers to a —COOH moiety.

As used herein, "carboxylate" or "carboxylates" refer to compounds having the general formula: R—COO$^-$, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "carboxylates" may refer to a group of compounds with the general formula described above, wherein the compounds have different carbon lengths. The term "carboxyl" can also refers to a —COO$^-$ moiety. In many instances, the carboxylate exists in the presence of a positively charged counterion. Examples of suitable counterions include, but are not limited to, alkali metal cations and alkaline earth metal cations.

As used herein, "alcohol" or "alcohols" refer to compounds having the general formula: R—OH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "alcohol" or "alcohols" may refer to a group of compounds with the general formula described above, wherein the compounds have different carbon lengths. The term "hydroxyl" refers to a —OH moiety.

As used herein, the "organophosphorus compound" refers to a compound containing a phosphorus atom bonded to one or more organic moieties. As used herein, "organic phosphine compound" or "organic phosphine compounds" refer to compounds having the general formula: $PR_3$, wherein R denotes a hydrogen atom or any organic moiety (such as alkyl, aryl, or silyl groups), including those bearing heteroatom-containing substituent groups, wherein at least one of the R groups is an organic moiety. In certain embodiments, R denotes alkyl, alkenyl, aryl, or alcohol groups. In certain embodiments, the term "organic phosphine compounds" may refer to a group of compounds with the general formula described above, wherein the compounds have different carbon lengths.

As used herein, "organic phosphonium compound" or "organic phosphonium compounds" refer to compounds having the general formula: $PR_4^+$, wherein R denotes a hydrogen atom or any organic moiety (such as alkyl, aryl, or silyl groups), including those bearing heteroatom-containing substituent groups, wherein at least one of the R groups is an organic moiety. In certain embodiments, R denotes alkyl, alkenyl, aryl, or alcohol groups. In certain embodiments, the term "organic phosphonium compounds" may refer to a group of compounds with the general formula described above, wherein the compounds have different carbon lengths. In some embodiments, the organic phosphonium compounds may exist in the presence of negatively charged counterions, such as halides, sulfates, phosphates, and the like.

As used herein, "organic phosphine oxide" or "organic phosphine oxides" refer to compounds having the general formula: $P(=O)R_3$, wherein R denotes a hydrogen atom, a hydroxyl group, or any organic moiety (such as alkyl, aryl, or silyl groups), including those bearing heteroatom-containing substituent groups, wherein at least one of the R groups is an organic moiety. In certain embodiments, R denotes alkyl, alkenyl, aryl, or alcohol groups. In certain embodiments, the term "organic phosphine oxides" may refer to a group of compounds with the general formula described above, wherein the compounds have different carbon lengths.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "$C_{x-y}$ alkyl," which refers to an alkyl group, as herein defined, containing from x to y, inclusive, carbon atoms. Thus, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group.

As used herein, "alkynyl" refers to a straight or branched chain non-aromatic hydrocarbon having 2 to 30 carbon atoms and having one or more carbon-carbon triple bonds, which may be optionally substituted, as herein further described, with multiple degrees of substitution being allowed. Examples of "alkynyl," as used herein, include, but are not limited to, ethynyl, 2-propynyl, 2-butynyl, and 3-butynyl. The number of carbon atoms in an alkynyl group is represented by the phrase "$C_{x-y}$ alkynyl," which refers to an alkynyl group, as herein defined, containing from x to y, inclusive, carbon atoms. Thus, "$C_{2-6}$ alkynyl" represents an alkynyl chain having from 2 to 6 carbon atoms and, for example, includes, but is not limited to, ethynyl, 2-propynyl, 2-butynyl, and 3-butynyl. In some instances, the "alkynyl" group can be divalent, in which case the group can alternatively be referred to as an "alkynylene" group.

As used herein, "cycloalkyl" refers to an aliphatic saturated or unsaturated hydrocarbon ring system having 1 to 20 carbon atoms, which may be optionally substituted, as herein further described, with multiple degrees of substitution being allowed. Examples of "cycloalkyl," as used herein, include, but are not limited to, cyclopropyl, cyclobutyl, cyclopentyl, cyclohexyl, cycloheptenyl, cyclohexenyl, cycloheptyl, cyclooctyl, adamantyl, and the like. The number of carbon atoms in a cycloalkyl group is represented by the phrase "$C_{x-y}$ cycloalkyl," which refers to a cycloalkyl group, as herein defined, containing from x to y, inclusive, carbon atoms. Thus, "$C_{3-10}$ cycloalkyl" represents a cycloalkyl having from 3 to 10 carbon atoms and, for example, includes, but is not limited to, cyclopropyl, cyclobutyl, cyclopentyl, cyclohexyl, cyclohexenyl, cycloheptyl, cyclooctyl, and adamantyl. In some instances, the "cycloalkyl" group can be divalent, in which case the group can alternatively be referred to as a "cycloalkylene" group.

As used herein, "alkoxy" refers to —OR, where R is an alkyl group (as defined above). The number of carbon atoms in an alkyl group is represented by the phrase "$C_{x-y}$ alkoxy," which refers to an alkoxy group having an alkyl group, as herein defined, containing from x to y, inclusive, carbon atoms.

As used herein, "halogen" or "halo" refers to a fluorine, chlorine, bromine, and/or iodine atom. In some embodiments, the terms refer to fluorine or chlorine atoms.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "aqueous medium" refers to a medium having a solvent or a matrix that contains water. In some embodiments, the aqueous medium is a solution, where the solvent contains water and, optionally, one or more other fluids that are miscible with water (e.g., methanol, ethanol, acetone, acetonitrile, and the like). In some other embodiments, the aqueous medium is a suspension or a dispersion, where the matrix material contains water and, optionally, one or more other fluids that are miscible with water. An aqueous medium having a pH greater than 7 can be referred to as a "basic medium," while an aqueous medium having a pH less than 7 can be referred to as an "acidic medium."

As used herein, "ionic strength" refers to the value calculated using the following formula:

$$I = \frac{1}{2}\sum_{i=1}^{n} b_i \cdot z_i^2$$

wherein: i represents each ion, b represents the molal concentration of the ion in the solution, and z represents the charge of the given ion.

As used herein, "yield" refers to the amount of reaction product formed in a reaction. When expressed with units of percent (%), the term yield refers to the amount of reaction product actually formed, as a percentage of the amount of reaction product that would be formed if all of the limiting reactant were converted into the product.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

This disclosure may incorporate one or more documents by reference. In such instances, the text of the document is incorporated into the text of this disclosure as though fully set forth herein. To the extent that an incorporated reference directly or indirectly contradicts the teachings of the present disclosure (e.g., different definitions for a term or phrase), the present disclosure shall control.

Other terms are defined in other portions of this description, even though not included in this subsection.

Refining Materials Derived from Renewable Sources

Renewable sources, such as natural oils and their derivatives, can provide useful starting materials for making a variety of chemical compounds and compositions. Various methods can be used to convert natural oils and/or their derivatives to such compounds and/or compositions. Useful methods include, but are not limited to, fermentation, other biological conversions, and metathesis.

Olefin metathesis can be used to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide new unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene and 1-decenoid acid (or an ester thereof), among other products, are formed. Following transesterification, for example, with an alkyl alcohol, an amount of 9-denenoic acid alkyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275595, and 2014/0275681, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene.

In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, the unsaturated esters may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, multiple metathesis reactions can also be employed. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The conditions for such metathesis reactions, and the reactor design, and suitable catalysts are as described above with reference to the metathesis of the olefin esters. That discussion is incorporated by reference as though fully set forth herein.

In the embodiments above, the natural oil (e.g., as a glyceride) is metathesized, followed by transesterification. In some other embodiments, transesterification can precede metathesis, such that the fatty acid esters subjected to metathesis are fatty acid esters of monohydric alcohols, such as methanol, ethanol, or isopropanol.

Olefin Metathesis

In some embodiments, one or more of the unsaturated monomers can be made by metathesizing a natural oil or natural oil derivative. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be used, depending on the desired product or product mixture.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linolenic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, the methods disclosed herein can employ multiple methathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments were a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The rector design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveda-Grubbs-type olefin metathesis catalyst and/or an entity derived therefrom. In some embodiments, the metathesis catalyst includes a second-generation Hoveda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than $-40°$ C., or greater than $-20°$ C., or greater than $0°$ C., or greater than $10°$ C. In certain embodiments, the metathesis reaction temperature is less than $200°$ C., or less than $150°$ C., or less than $120°$ C. In some embodiments, the metathesis reaction temperature is between $0°$ C. and $150°$ C., or is between $10°$ C. and $120°$ C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

Biorefineries Incorporating Olefin Metathesis

Olefin metathesis can be incorporated into a biorefinery, where larger-scale amounts of a natural oil and/or its derivatives are metathesized, and the resulting product streams are collected. Non-limiting examples of biorefineries incorporating olefin metathesis are described in United States Patent Application Publication No. 2013/0204022, which is hereby incorporated by reference as though fully set forth herein.

FIG. 1 describes an illustrative embodiment for incorporating olefin metathesis into a biorefinery. A natural oil or natural oil derivative 12 is reacted with a low-molecular-weight olefin 14 or mid-weight olefin 15 in a metathesis reactor 20 in the presence of a metathesis catalyst. Metathesis catalysts and metathesis reaction conditions are discussed in greater detail above. The metathesis reactions form, among other products, a metathesized product 22 wherein the metathesized product 22 comprises olefins 32 and esters 34. In some embodiments, the olefins 32 are alkenes, such as terminal alkenes or internal alkenes. In some embodiments, the esters 34 are olefin esters, such as terminal olefin esters or internal olefin esters. In some such embodiments, the esters are glycerides. In some other embodiments, the esters are esters of simple monohydric alcohols (e.g., methanol, ethanol, isopropanol, butanol, and the like).

In some embodiments, the low-molecular-weight olefin 14 is in the $C_{2-6}$ range. As a non-limiting example, in some embodiments, the low-molecular-weight olefin 14 may comprise at least one of the following: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-9}$ range include 1,4-heptadiene, 1-heptene, 3,6-nonadiene, 3-nonene, 1,4,7-octatriene. In another embodiment, the low-molecular-weight olefin 14 comprises at least one of styrene or vinyl cyclohexane. In some other embodiments, the low-molecular-weight olefin 14 may comprise at least one of ethylene, propylene, 1-butene, 2-butene, and isobutene. In some other embodiments, the low-molecular-weight olefin 14 comprises at least one alpha-olefin or terminal olefin in the $C_{2-10}$ range. In some such embodiments, the low-molecular-weight olefin 14 comprises at least one alpha-olefin or terminal olefin in the $C_{2-4}$ range, such as ethylene, propylene, or 1-butene. In some embodiments, the low-molecular-weight olefin 14 comprises ethylene. In some other embodiments, the low-molecular-weight olefin 14 comprises 1-butene. In some other embodiments, the low-molecular-weight olefin 14 comprises 2-butene.

In some other embodiments, the low-molecular-weight olefin 14 comprises at least one branched low-molecular-weight olefin in the $C_{4-10}$ range. Non-limiting examples of branched low-molecular-weight olefins include isobutene, 3-methyl-1-butene, 2-methyl-3-pentene, and 2,2-dimethyl-3-pentene.

In some embodiments where a mid-weight olefin 15 is used in the metathesis process, the mid-weight olefin 15 comprises unsaturated straight, branched, or cyclic hydrocarbons in the $C_{15-24}$ range. In some embodiments, the mid-weight olefin is an alpha-olefin or terminal olefin. In some embodiments, no mid-weight olefin is used.

It can be possible to use a mixture of various linear or branched low-molecular-weight olefins and linear or branched mid-weight olefins in the reaction to achieve the desired metathesis product distribution. In some embodiments, the mixture comprises linear and/or branched low-molecular-weight olefins. In some other embodiments, the mixture comprises linear and/or branched mid-weight olefins. In some embodiments, a mixture of butenes (1-butene, 2-butenes, and, optionally, isobutene) may be employed as the low-molecular-weight olefin, offering a low-cost, commercially available feedstock instead a purified source of one particular butene. Such low-cost mixed butene feedstocks can, in some embodiments, be diluted with n-butane and/or isobutene.

In some embodiments, recycled streams from downstream separation units may be introduced to the metathesis reactor 20 in addition to the natural oil or natural oil derivative 12 and, in some embodiments, the low-molecular-weight olefin 14 and/or mid-weight olefin 15. For instance, in some embodiments, a $C_{2-6}$ recycle olefin stream or a $C_{3-4}$ bottoms stream from an overhead separation unit may be returned to the metathesis reactor. In some embodiments, as shown in FIG. 1, a light-weight olefin stream 44 from an olefin separation unit 40 may be returned to the metathesis reactor 20. In some other embodiments, the $C_{3-4}$ bottoms stream and the light-weight olefin stream 44 are combined together and returned to the metathesis reactor 20. In some other embodiments, a $C_{15+}$ bottoms stream 46 from the olefin separation unit 40 is returned to the metathesis reactor 20. In some other embodiments, all of the aforementioned recycle streams are returned to the metathesis reactor 20.

In some embodiments, various ester streams downstream of the transesterification unit (discussed below) may also be recycled or returned to the metathesis reactor 20. In some embodiments, a glycerolysis reaction may be conducted on the recycled ester stream to prevent or limit the amount of free glycerol entering the metathesis reactor 20. In some embodiments, the recycled ester stream undergoes a purification step to limit the amount of methanol being recycled to the metathesis reactor 20. In some embodiments, the recycled ester stream is combined with the low-molecular-weight olefin 14 and/or mid-weight olefin 15 prior to conducting the glycerolysis reaction and entering the metathesis reactor 20. In some embodiments, the glycerolysis reaction may also limit or prevent free fatty acid methyl esters from entering the metathesis reaction and subsequently exiting the metathesis reactor as free fatty acid methyl esters that may boil close to various high-valued olefin products. In some such cases, these methyl ester components may be separated with the olefins during the separation of the olefins and esters. In some instances, such methyl ester components may be difficult to separate from the olefins by distillation.

The metathesis reaction in the metathesis reactor 20 produces a metathesized product 22. In some embodiments, the metathesized product 22 enters a flash vessel operated under temperature and pressure conditions that target $C_2$ or $C_{2-3}$ compounds to flash off and be removed overhead. The $C_2$ or $C_{2-3}$ light ends mainly include hydrocarbon compounds having a carbon number of 2 or 3. In some embodiments, the $C_2$ or $C_{2-3}$ light ends are then sent to an overhead separation unit, wherein the $C_2$ or $C_{2-3}$ compounds are further separated overhead from the heavier compounds that may have flashed off with the $C_2$ or $C_{2-3}$ compounds. These heavier compounds are typically $C_{3-5}$ compounds carried overhead with the $C_2$ or $C_{2-3}$ compounds. In some embodiments, after separation in the overhead separation unit, the overhead $C_2$ or $C_{2-3}$ stream may be collected and used as a fuel source. These hydrocarbons may, however, have their own value outside the scope of a fuel composition, and, in some embodiments, may be used or separated at this stage for use in other compositions and applications. In some embodiments, the bottoms stream from the overhead separation unit containing mostly $C_{3-5}$ compounds is returned as a recycle stream to the metathesis reactor. In some embodiments, the metathesized product 22 that does not flash overhead in the flash vessel is sent downstream for separation in a separation unit 30, such as a distillation column.

Prior to the separation unit 30, in certain embodiments, the metathesized product 22 may be contacted with a reactant or reagent to deactivate or to extract the catalyst. In certain embodiments, the metathesized product 22 is introduced to an agent, such as an adsorbent or complexing agent, to facilitate the separation of the metathesized product 22 from the metathesis catalyst. In some embodiments, the agent is a clay bed. In some such embodiments, the clay bed can adsorb the metathesis catalyst, and after a filtration step, the metathesized product 22 can be sent to the separation unit 30 for further processing. In some other embodiments, the agent is an organophosphorus compound, such as an organic phosphine compound or an organic phosphonium compound. In some embodiments, such phosphine or phosphonium compounds are at least partially soluble in water. In some embodiments, the organic phosphine compound is tris(hydroxymethyl)phosphine (THMP).

The phosphine and/or phosphonium compounds can be generated in any suitable manner. In some embodiments, they can be introduced directly into a composition comprising the metathesized product composition. For example, in some embodiments, a phosphonium salt (e.g., a halide or sulfate salt) can be added. In some such embodiments, the phosphonium cation is tetrakis(hydroxymethyl)phosphonium. The phosphonium compounds may, in certain instances, convert to phosphine compounds, for example, when introduced to an aqueous medium at a suitable pH. Thus, in some embodiments where a phosphonium salt is introduced to a composition comprising the metathesized product composition, at least a portion of the introduced phosphonium salt converts to a corresponding phosphine compound, e.g., tris(hydroxymethyl)phosphine. Thus, in some embodiments, the phosphine or phosphonium compound can be generated in situ via conversion from another compound.

In some instances, the organophosphorus compounds can be used to kill the catalytic activity of the metathesis catalyst or any metathesis catalyst residues. Because metathesis reactions conserve the number of carbon-carbon double bonds, any products formed from a metathesis reaction can also serve as reactants for further metathesis reactions. Thus, as long as there is available catalyst in the reactor, metathesis reactions will continue to occur. In some instances, such as where the products of these follow-on metathesis reactions are less valuable, it may be desirable to stop further reactions from occurring. In some embodiments, the metathesis reactions can be "killed" by contacting the metathesis catalyst with an organophosphorus compound. In such instances, the organophosphorus compound can react with the catalyst complex and transform it in a manner that reduces or eliminates its ability to catalyze further metathesis reactions. In addition, certain metathesis catalyst residues may serve as catalysts for other undesirable reactions, such as olefin isomerization reactions. Thus, in some embodiments, organophosphorus compounds can also be used to kill the catalytic activity of such metathesis catalyst residues.

The organophosphorus compounds can be introduced in any suitable manner. In some embodiments, the organophosphorus compounds can be introduced directly into the metathesis reactor. In some other embodiments, however, at least a portion of the metathesized product composition 22, including any metathesis catalyst and/or metathesis catalyst residues, can be transferred to a separate vessel, e.g., a kill drum, where the organophosphorus compounds are introduced.

The organophosphorus compounds can be used in any suitable amount relative to the amount of catalyst or catalyst resides to be deactivated. For example, the mole-to-mole of organophosphorus compounds to catalyst or catalyst resides can range from 1:5 to 500:1, or from 1:1 to 100:1, or from 2:1 to 50:1. In some embodiments, the mole-to-mole of organophosphorus compounds to catalyst or catalyst resides is at least 1:1, or at least 5:1, or at least 10:1, or at least 25:1, or at least 50:1.

In some instances, it can be desirable to remove the passivated catalyst or catalyst residues and any organophosphorus compounds from the metathesized product. In many instances, the products of metathesizing a natural oil or natural oil derivative are not highly soluble in water, while the catalyst, catalyst residues, organophosphorus compounds, and other impurities are. Therefore, in some embodiments, the metathesized product composition can be washed with a polar solvent (e.g., an aqueous medium) following catalyst passivation. This can be done by any suitable means. For example, in some embodiments, at least a portion of the composition from the catalyst kill drum is transferred to another vessel, such as a decanter drum. In some embodiments, the decanter drum may function as a horizontal vessel with a vertical baffle and a boot to collect the water phase containing the metathesis catalyst. The decanter drum can be operated at any suitable temperature and pressure. In some embodiments, the decanter drum operates at a temperature of 50 to 90° C. and a pressure between of 1 to 15 atm, or 1 to 10 atm, or 1 to 5 atm, or 1 to 2 atm. In some embodiments, the decanter drum operates at about 53° C. and about 1.1 atm.

In other embodiments, the metathesized product composition is treated by washing or extracting the mixture with a polar solvent (e.g., an aqueous medium). In some embodiments, the polar solvent is introduced following catalyst deactivation or passivation. In some other embodiments, the polar solvent is added to the metathesized product 22 at approximately the same time as the deactivation reagent (e.g., an organophosphorus compound, such as THMP). Near simultaneous introduction of the organophosphorus compound and the polar solvent to the metathesized product can, in some embodiments, eliminate the need for an additional reaction/separation vessel, which may simplify the process and may reduce the costs associated with the process.

In some embodiments, the polar solvent is at least partially non-miscible with the metathesized product composition, such that a separation of layers can occur. In some embodiments, at least a portion of the organophosphorus compounds and/or the catalyst or catalyst residues are partitioned into the polar solvent layer, which can then be separated from the non-miscible remaining layer and removed. In some embodiments, the separated polar medium is an aqueous composition comprising: (i) an organic phosphine compound or an organic phosphonium compound, and (ii) a metathesis catalyst residue, the treatment of which is described in further detail below.

Any suitable polar solvent or solvent system can be used. Suitable polar solvents include, but are not limited to, water, alcohols (e.g., methanol, ethanol, etc.), ethylene glycol, glycerol, dimethyl formamide (DMF), multifunctional polar compounds, such as polyethylene glycols and/or glymes, ionic liquids, and the like, and any combinations thereof. In some embodiments, polar solvent primarily comprises water.

The extracting or washing of the metathesized product with a polar solvent can be carried out in any suitable manner. In some embodiments, the extracting comprises high shear mixing (e.g., mixing of a type sufficient to disperse and/or transport at least a portion of a first phase and/or chemical species into a second phase with which the first phase and/or a chemical species would normally be at least partly immiscible) although such mixing, in some embodiments, may contribute to undesirable emulsion formation. In some embodiments, the extracting comprises low-intensity mixing (e.g., stirring that is not high shear). Mixing can be carried out by any suitable means for any suitable duration. For example, in some embodiments, the extracting comprises mixing the polar solvent and the metathesized product together for at least 1 second, or at least 10 seconds, or at least 30 seconds, or at least 1 minute, or at least 2 minutes, or at least 5 minutes, or at least 10 minutes, or at least 15 minutes, or at least 20 minutes, or at least 25 minutes, or at least 30 minutes, or at least 35 minutes, or at least 40 minutes, or at least 45 minutes, or at least 50 minutes, or at least 55 minutes, or at least 1 hour, or at least 2 hours, or at least 3 hours, or at least 4 hours. In some embodiments, however, the mixing is carried out for no more than 30 seconds, or no more than 1 minute, or no more than 2 minutes, especially, for example, in instances where inline shear mixing is used.

Any suitable amount of polar solvent can be used to carry out the extracting or washing. In some embodiments, the weight-to-weight ratio of the introduced polar solvent to the metathesized product composition is at least 1:100 or at least 1:50, or at least 1:20, or at least 1:10, or at least 1:5, or at least 1:1. In some embodiments, the weight-to-weight ratio of the introduced polar solvent to the metathesized product composition ranges from 1:100 to 100:1, or from 1:100 to 10:1, or from 1:100 to 1:1, or from 1:100 to 1:2. In some embodiments, such as where the ratio of polar solvent to oil is lower, extraction and separation can be carried out using a centrifuge and/or coalescer.

In some embodiments, it may be desirable to minimize dehydrogenation during the extraction or washing process. Thus, in some embodiments, the methods include allowing a settling period following the polar solvent wash/mixing to promote phase separation. Any suitable setline period can be used. For example, in some embodiments, the settling period is at least 1 minute, or at least 2 minutes, or at least 5 minutes, or at least 10 minutes, or at least 15 minutes, or at least 30 minutes, or at least 60 minutes, or at least 120 minutes.

In some alternative embodiments, other methods can be employed in addition to or as an alternative to washing/extracting. For example, in some embodiments, the passivated metathesis product composition can be treated by introducing an adsorbent, which optionally can then be physically separated from the mixture (e.g., via filtration, centrifugation, crystallization, or the like). In some embodiments, the adsorbent is polar. Suitable adsorbents include, but are not limited to, carbon, silica, silica-alumina, alumina, clay, magnesium silicates (e.g., magnesols), synthetic silica-based adsorbents (e.g., TRISYL, W. R. Grace & Co.) diatomaceous earth, polystyrene, macroporous (MP) resins, and the like, and combinations thereof. In some embodiments, the adsorbents can be washed with a polar solvent (e.g., an aqueous medium) to extract at least a portion of any adsorbed organophosphorus compounds and/or catalyst or catalyst residue. In some embodiments, the resulting medium is an aqueous composition comprising: (i) an organic phosphine compound or an organic phosphonium compound, and (ii) a metathesis catalyst residue, the treatment of which is described in further detail below.

Treatment of Biorefinery Wash Streams

As noted above, various methods can be used to remove at least a portion of the organophosphorus compounds, catalyst, and/or catalyst residue from the passivated metathesized product composition. In general, these methods result in an aqueous composition comprising: (i) an organic phosphine compound or an organic phosphonium compound, and (ii) a metathesis catalyst residue. As described in further detail below, such wash streams can also include other water-soluble impurities that were removed from the metathesized product composition. Such additional impurities include low-molecular-weight organic compounds, such as formaldehyde.

To the extent that any of the components of the wash stream are valuable, it may be desirable to seek to recover at least a portion of such species from the wash stream. For example, in some embodiments, at least a portion of the catalyst residues (or derivatives thereof) are recovered from the wash stream. Meanwhile, the wash stream may also contain materials that are not worth recovering, but which may be too toxic to be disposed of through conventional low-cost means. Therefore, it can also be desirable to treat the wash stream in a manner so as to convert certain species in the wash stream to less toxic variants. In some embodiments, these two goals can be coupled together into a single method.

The methods disclosed herein include: providing a first polar medium comprising (i) an organic phosphine compound or an organic phosphonium compound, and (ii) a metathesis catalyst residue; and reacting the organic phosphine compound or the organic phosphonium compound with an oxidizing agent to form a second aqueous medium comprising an organic phosphine oxide.

As used herein, "providing" refers broadly to any generation of the polar medium, including, but not limited to, generating the polar medium by means of any of the above-referenced washing or extraction methods. As used herein, the "providing" can, in some instances, be integrated with the subsequent steps in the method, or the "providing" may not be integrated with the subsequent steps in the process.

In some embodiments, the first polar medium comprises a polar medium generated from a wash and/or extraction of a metathesized natural oil or a metathesized natural oil derivative with a polar medium, e.g., the wash and/or extraction of a metathesis product composition (described above). In some embodiments, the metathesis product composition is generated in a biorefinery.

In some embodiments, where the first polar medium comprises a polar medium generated from a wash and/or extraction of a metathesized natural oil or a metathesized natural oil derivative, the first polar medium is the wash and/or extraction stream itself, e.g., without any further addition of other components. In some other embodiments, the wash and/or extraction stream can me modified before its incorporation into the methods disclosed herein. For example, in some embodiments, one or more additional ingredients are added to the wash/extraction composition, including, but not limited to, one or more additional solvents (e.g., water or other polar solvents), and one or more other compounds, such as surfactants, pH modifiers or buffers, complexing agents, and the like. In some embodiments, the wash/extraction can be treated. Suitable treatment methods include, but are not limited to, evaporating, filtering, mixing, and the like.

The first polar medium can employ any suitable solvent system. In some embodiments, the polar medium is an aqueous medium, meaning that the solvent system comprises water. In some embodiments, the solvent system is at least 30% by weight, or at least 50% by weight, or at least 60% by weight, or at least 70% by weight, or at least 80% by weight, or at least 90% by weight, or at least 95% by weight, water. In some such embodiments, other solvents can be present, such as one or more additional solvents that are miscible with water. Suitable water-miscible solvents include, but are not limited to, methanol, ethanol, isopropanol, diols, triols, amines such as ethylamine, 1,4-dioxane, tetrahydrofuran (THF), acetone, acetonitrile, and the like.

In some embodiments, the first polar medium is an aqueous medium. In some embodiments, the aqueous medium comprises an organic phosphine compound or an organic phosphonium compound. In embodiments where the aqueous medium comprises a metathesis biorefinery wash/extraction stream, one or both of these phosphorus-based compounds can be present due to their use, for example, as agents to kill the metathesis catalyst (described in more detail above). The polar medium can contain any combination of phosphine and/or phosphonium compounds.

In some embodiments, the phosphine compound is an organic phosphine compound. In some such embodiments, the organic phosphine compound is a compound according to formula (Ia):

(Ia)

wherein $R^1$, $R^2$, and $R^3$ are independently a hydrogen atom or a $C_{1-20}$ hydrocarbyl group, wherein one or more of the carbon atoms in the hydrocarbyl group can be replaced by a heteroatom selected from the group consisting of nitrogen, oxygen, sulfur, and oxidized forms thereof; and wherein at least one of $R^1$, $R^2$, and $R^3$ is not a hydrogen atom. In some such embodiments, $R^1$, $R^2$, and $R^3$ are independently $C_{1-12}$ alkyl, which is optionally substituted one or more times by substituents selected independently from —OH, —O($C_{1-6}$ alkyl), —$NH_2$, —NH($C_{1-6}$ alkyl), —N($C_{1-6}$ alkyl)$_2$, and a halogen atom. In some other such embodiments, $R^1$, $R^2$, and $R^3$ are independently $C_{1-8}$ alkyl, which is optionally substituted one or more times by —OH. In some further such embodiments, $R^1$, $R^2$, and $R^3$ are —$CH_2$—OH. In some embodiments, the phosphine compound was generated via a conversion of a phosphonium compound to a phosphine compound.

In some embodiments, the phosphonium compound is an organic phosphonium compound. In some such embodiments, the organic phosphonium compound (cation) is a compound according to formula (Ib):

wherein $R^4$, $R^5$, $R^6$, and $R^7$ are independently a hydrogen atom or a $C_{1-20}$ hydrocarbyl group, wherein one or more of the carbon atoms in the hydrocarbyl group can be replaced by a heteroatom selected from the group consisting of nitrogen, oxygen, sulfur, and oxidized forms thereof; and wherein at least one of $R^4$, $R^5$, $R^6$, and $R^7$ is not a hydrogen atom. In some such embodiments, $R^4$, $R^5$, $R^6$, and $R^7$ are independently $C_{1-12}$ alkyl, which is optionally substituted one or more times by substituents selected independently from —OH, —O($C_{1-6}$ alkyl), —$NH_2$, —NH($C_{1-6}$ alkyl), —N($C_{1-6}$ alkyl)$_2$, and a halogen atom. In some other such embodiments, $R^4$, $R^5$, $R^6$, and $R^7$ are independently $C_{1-8}$ alkyl, which is optionally substituted one or more times by —OH. In some further such embodiments, $R^4$, $R^5$, $R^6$, and $R^7$ are —$CH_2$—OH.

In some embodiments, where the polar medium comprises one or more phosphonium compounds, the polar medium can also comprise one or more counterions (anions) to the phosphonium cation. Any suitable cations can be employed. In some embodiments, counterions can form via the acid-base equilibrium of one or more of the solvents, e.g., generation of hydroxide anions from water. Other anions can also be present, including, but not limited to, halide anions, sulfate anions, hydrogen sulfate anions, phosphate anions, hydrogen phosphate anions, dihydrogen phosphate anions, nitrate anions, hydroxide anions, carbonate anions, hydrogen carbonate anions, cyanide anions, acetate anions, formate anions, oxalate anions, and any mixtures thereof. In some embodiments, the one or more counteranions are selected from the group consisting of: a chloride anion, a sulfate anion, and any mixtures thereof.

The first polar medium can, in some embodiments, comprise certain metathesis catalyst resides. As noted above, such metathesis catalyst residues are compounds derived directly or indirectly from a metathesis catalyst. In some instances, at least a portion of the metathesis catalyst residues are compounds formed from the reaction of the metathesis catalyst and the phosphine or phosphonium compounds. In some instances, at least a portion of the metathesis catalyst residues are formed by transforming the metathesis catalyst during the catalysis of a metathesis reaction to form a derivative of the metathesis catalyst, which is then reacted with the phosphine or phosphonium compound to form the metathesis catalyst residues. As noted above, any suitable metathesis catalysts can be used. In some embodiments, however, the catalyst is a ruthenium alkylidene catalyst, including, but not limited to, a Grubbs Generation I metathesis catalyst, a Grubbs Generation II metathesis catalyst, or a Grubbs-Hoveyda Generation II metathesis catalyst.

In some embodiments, the method includes separating at least a portion of the metathesis catalyst residue from the first polar medium. This can be done by any suitable means. The selection of the means can depend on a variety of factors. In some embodiments, a precipitating agent can be introduced to the polar medium, which causes at least a portion of the catalyst resides to be converted to compounds that are less soluble in the polar medium. Any formed precipitate can be removed via physical separation means, e.g., filtration. In some other embodiments, a less polar solvent system can be introduced to the polar medium to form a multi-phase system, and at least a portion of the metathesis catalyst residues are extracted into less polar solvent system. In some such embodiments, at least a portion of the metathesis catalyst residues may be chemically converted to one or more other residue compounds, so as to make them more soluble in the less polar phase than the more polar phase and thereby enhancing the amount extracted into the less polar solvent system.

Any suitable amount of the metathesis catalyst residues can be separated from the polar medium. For example, in some embodiments, at least 30% by weight, or at least 40% by weight, or at least 50% by weight, or at least 60% by weight, or at least 70% by weight, or at least 80% by weight, or at least 90% by weight of the metathesis catalyst residue is separated from the first polar medium, based on the total weight of metathesis catalyst residue present in the first polar medium.

The first polar medium can contain one or more additional compounds that are extracted from the metathesis product composition, for example, undesired byproducts of the metathesis reactions. In some embodiments, the first polar medium contains one or more aldehydes, such as formaldehyde. Other such undesired byproducts can also be present.

The methods disclosed herein include reacting the organic phosphine compound or the organic phosphonium compound (or both, if present) with an oxidizing agent to form a second polar medium comprising an organic phosphine oxide.

The second polar medium can also contain an amount of metathesis catalyst residues. For example, in some embodiments, the optional catalyst residue separation step is not performed, thereby leaving most or all of the metathesis catalyst residues in the polar medium following introduction of the oxidizing agent. In some other embodiments, the above-described separating step can leave some amount of the metathesis catalyst residues in the polar medium, such that an amount of metathesis catalyst residues remain in the polar medium following introduction of the oxidizing agent. In some such embodiments, an amount of the metathesis catalyst resides can be separated from the second polar medium. Any suitable method can be used to effect such separation, including, but not limited to, the methods described above. Any suitable amount of the metathesis catalyst residues can be separated. For example, in some embodiments, at least 30% by weight, or at least 40% by weight, or at least 50% by weight, or at least 60% by weight, or at least 70% by weight, or at least 80% by weight, or at least 90% by weight of the metathesis catalyst residue is separated from the first polar medium, based on the total weight of metathesis catalyst residue present in the second polar medium.

As noted above, the disclosed method includes introduction of an oxidizing agent. Any oxidizing agent or combination of oxidizing agents suitable for use in a polar solvent system, such as water, can be used. For example, in some embodiments, the oxidizing agent is an organic oxidizing agent, including, but not limited to, an organic peroxide. In some other embodiments, the oxidizing agent is an inorganic oxidizing agent, including, but not limited to, hydrogen peroxide, another inorganic peroxide, oxygen, ozone, a hypochlorite, a chlorate, nitric acid, chromium trioxide, a chromate, a dichromate, a manganite, a permanganate, or any combinations thereof.

The oxidation reaction can occur in a medium having any suitable pH. In some embodiments, however, the reacting occurs in a basic medium. In some such embodiments, the basic medium has a pH of from 8 to 12. In some embodiments, the basic medium includes an amount of a strong inorganic base. Such strong inorganic bases include, but are not limited to, a hydroxide, a basic ion exchange resin, or a solid base.

The reacting oxidizes a substantial portion of the phosphine and/or phosphonium compounds to phosphine oxide compounds. The resulting phosphine oxide compounds can have any suitable chemical structure. In some embodiments, the resulting phosphine oxide compounds are compounds of formula (Ic):

wherein $R^8$, $R^9$, and $R^{10}$ are independently a hydrogen atom or a $C_{1-20}$ hydrocarbyl group, wherein one or more of the carbon atoms in the hydrocarbyl group can be replaced by a heteroatom selected from the group consisting of nitrogen, oxygen, sulfur, and oxidized forms thereof, or any two of $R^8$, $R^9$, and $R^{10}$ can optionally combine to form an oxide moiety (i.e., a =O group); and wherein at least one of $R^8$, $R^9$, and $R^{10}$ is not a hydrogen atom. In some such embodiments, $R^8$, $R^9$, and $R^{10}$ are independently $C_{1-12}$ alkyl, which is optionally substituted one or more times by substituents selected independently from —OH, —O($C_{1-6}$ alkyl), —NH$_2$, —NH($C_{1-6}$ alkyl), —N($C_{1-6}$ alkyl)$_2$, and a halogen atom. In some other such embodiments, $R^8$, $R^9$, and $R^{10}$ are independently $C_{1-8}$ alkyl, which is optionally substituted one or more times by —OH. In some further such embodiments, $R^8$, $R^9$, and $R^{10}$ are —CH$_2$—OH. Other phosphine oxide compounds can also be present following the oxidation.

In some embodiments, a substantial portion of the phosphine or phosphonium compounds in the polar medium are oxidized to phosphine oxide compounds. For example, in some embodiments, at least 70% by weight, or at least 80% by weight, or at least 90% by weight, or at least 95% by weight, or at least 97% by weight, or at least 98% by weight, or at least 99% by weight, of the collective amount of phosphine and phosphonium compounds in the first polar medium are oxidized, based on the total collective amount of phosphine and phosphonium compounds in the first polar medium.

As noted above, other compounds can be present in the polar medium, such as certain aldehydes, e.g., formaldehyde. At least a portion of these compounds can also be oxidized in the course of the reacting. For example, in some embodiments, the reacting can include reacting the aldehyde (e.g., formaldehyde) with the oxidizing agent to form (i) an alcohol (e.g., methanol), and (ii) a carboxylic acid, a carboxylate, or a mixture thereof (e.g., formic acid, formats, or mixtures thereof).

The second polar medium can optionally be subjected to further chemical and/or physical treatment. For example, in some embodiments, the second polar medium undergoes further chemical treatment following the oxidation.

In some embodiments, the chemical treatment includes adjusting the pH of the polar medium. In some such embodiments, the treatment includes adjusting the pH to a pH of from 5 to 9, or from 5 to 8, or from 6 to 8, or from 6.5 to 7.5. In some embodiments where the pH of the second polar medium (prior to any further chemical treatment), the treatment includes reducing the alkalinity of the medium. For example, in some embodiments, the treatment includes lowering the pH of the medium from a higher pH to a pH of from 5 to 8, or from 6 to 8, or from 6.5 to 7.5. In such embodiments, the treatment can include introducing one or more acids to the polar medium. The acid(s) can be added in any suitable manner. For example, in some embodiments, the acid can be introduced as part of a solid composition. In some other embodiments, however, the acid can be introduced as part of a liquid medium, e.g., a polar medium, such as an aqueous medium. Any suitable acid(s) can be used. For example, in some embodiments, the acid is an organic acid, an inorganic acid, an acidic ion exchange resin, or a solid acid, such as sulfonated zirconia, or any combination thereof. Examples include, but are not limited to, phosphoric acid, hydrochloric acid, sulfuric acid, and acetic acid.

In some embodiments, the treatment can include introducing one or more additional compounds or compositions to the polar medium. In embodiments where such further treatment is combined with acidification, this can occur before, during, or after acidification. Any suitable additional compounds and/or compositions can be added, including, but not limited to, solvents, surfactants, ionic species (e.g., salts), acids, bases, and the like.

In some such embodiments, the additional treatment includes introducing an anionic species, e.g., a sulfur-containing anionic species, to the polar medium. In some such embodiments, the anionic species are sulfites. The sulfites can be added in any suitable form. For example, in some embodiments, sulfites can be added directly to the composition, e.g., by adding a sulfite solution or a sulfite salt to the composition. In some embodiments, however, the sulfites can be introduced indirectly by introducing a species that can generate a sulfite anion in solution.

In some embodiments, the additional treatment can include introducing one or more species that may cause or enhance decomposition of any residual peroxide in the medium. For example, in some embodiments, the additional treatment includes introducing one or more peroxide decomposition catalysts to the polar medium. Any suitable peroxide decomposition catalysts can be used, including, but not limited to, transition metals, transition metal complexes, and combinations thereof. In some embodiments, the peroxide decomposition catalyst is palladium, platinum, silver, manganese dioxide, or a combination thereof. Such metals or compounds can be free or supported. In some embodiments, for example, one or more of the peroxide decomposition catalysts is supported. Any suitable solid support can be used, according to the knowledge of those of skill in the art.

In some instances, it may be desirable to ensure that certain properties of the polar medium are maintained during the course of any chemical or physical treatment. For example, in some embodiments, the treating does not substantially increase the ionic strength of the second polar medium. In some such embodiments, the treating does increases the ion strength of the second polar (e.g., aqueous) medium to a value no more than 0.3 molal, or no more than 0.2 molal, or no more than 0.1 molal, or no more than 0.05 molal.

In some embodiments, it can be desirable to prevent the temperature of the medium from increasing to an unreasonable degree, e.g., either by introduction of a heat source, or by generating heat from one or more chemical reactions. For example, in some embodiments, the treating causes the temperature of the second polar medium to increase by no more than 30° C., or no more than 20° C., or no more than 10° C.

The treating can also include removing at least a portion of one or more components of the polar medium. For example, in embodiments where the second polar medium includes water, at least a portion of the water is removed or separated from other components of the second polar medium. In some such embodiments, the removal or separation of the water results in a first stream comprising the removed or separated water and a second stream comprising other components of the second polar medium at higher concentrations (e.g., a concentrated treated polar (or aqueous) medium). This removal or separation can be done by any suitable means, depending on a variety of factors, including, but not limited to, the nature of the species being removed. In some embodiments, one or more components (e.g., water) are removed or separated from the polar medium by evaporation. In embodiments where the removed or separated stream includes water, the removed or separated water stream can be used to carry out a subsequent washing of a metathesized product composition (e.g., either by itself or in combination with one or more other ingredients). In other words, the separated or removed water stream can be recycled for re-use in a metathesis reactor.

Figure 2:
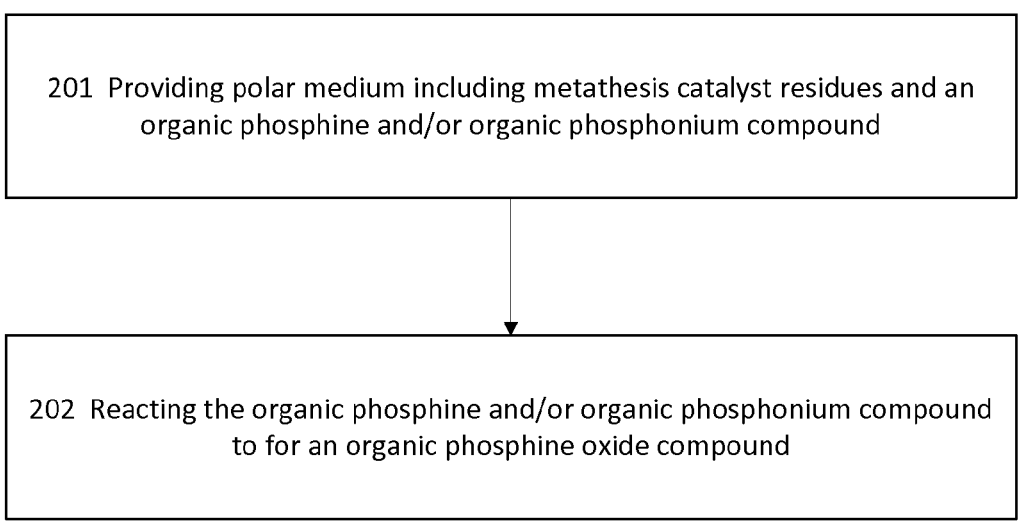
FIG. 2 shows an illustrative embodiment of treating a wastewater stream.

FIG. 2 illustrates some embodiments of the methods disclosed herein. In such embodiments, the methods 200 include: providing a polar (or aqueous) medium that contains metathesis catalyst residues and organic phosphine and/or organic phosphonium compounds 201; and reacting the organic phosphine and/or organic phosphonium compounds in the polar medium to form organic phosphine oxide compounds 202. Other optional steps can also be included. For example, in some embodiments, at least a portion of the catalyst residues are recovered from the polar medium after the providing 201 and before the reacting 202. In some other embodiments, at least a portion of the catalyst residues are recovered from the polar medium after the reacting 202, which may be done instead of an earlier catalyst residue recovery step or in combination with an earlier catalyst residue recovery step. Further, it should be noted that the reacting 202 can also include oxidizing other species in the polar medium that may be susceptible to oxidation. For example, in some embodiments, one or more aldehydes (e.g., formaldehyde) can be present in the polar medium, which are oxidized to alcohols (e.g., methanol) and acids (e.g., formic acid) in the reacting 202.

Figure 3:
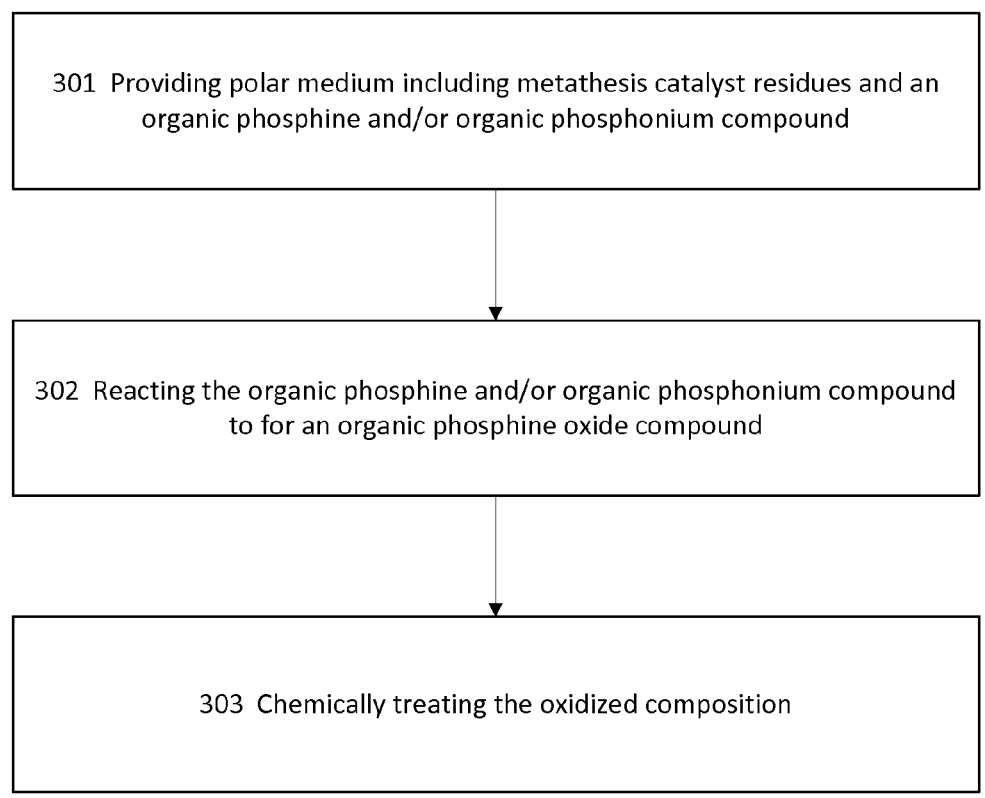
FIG. 3 shows an illustrative embodiment of treating a wastewater stream.

FIG. 3 illustrates some embodiments of the methods disclosed herein. In such embodiments, the methods 300 include: providing a polar (or aqueous) medium that contains metathesis catalyst residues and organic phosphine and/or organic phosphonium compounds 301; reacting the organic phosphine and/or organic phosphonium compounds in the polar medium to form organic phosphine oxide compounds 302; and chemically treating the oxidized composition (e.g., from the reacting 302) 303. The chemical treatment can include various treatments or combinations of treatments, including, but not limited to, adjusting the pH (e.g., to be less alkaline), introducing various anions (e.g., sulfites), and introducing compounds to break down or assist in breaking down any residual peroxides. Other optional steps can also be included. For example, in some embodiments, at least a portion of the catalyst residues are recovered from the polar medium after the providing 301 and before the reacting 302. In some other embodiments, at least a portion of the catalyst residues are recovered from the polar medium after the reacting 302, which may be done instead of an earlier catalyst residue recovery step or in combination with an earlier catalyst residue recovery step. Further, it should be noted that the reacting 302 can also include oxidizing other species in the polar medium that may be susceptible to oxidation. For example, in some embodiments, one or more aldehydes (e.g., formaldehyde) can be present in the polar medium, which are oxidized to alcohols (e.g., methanol) and acids (e.g., formic acid) in the reacting 302.

Figure 4:
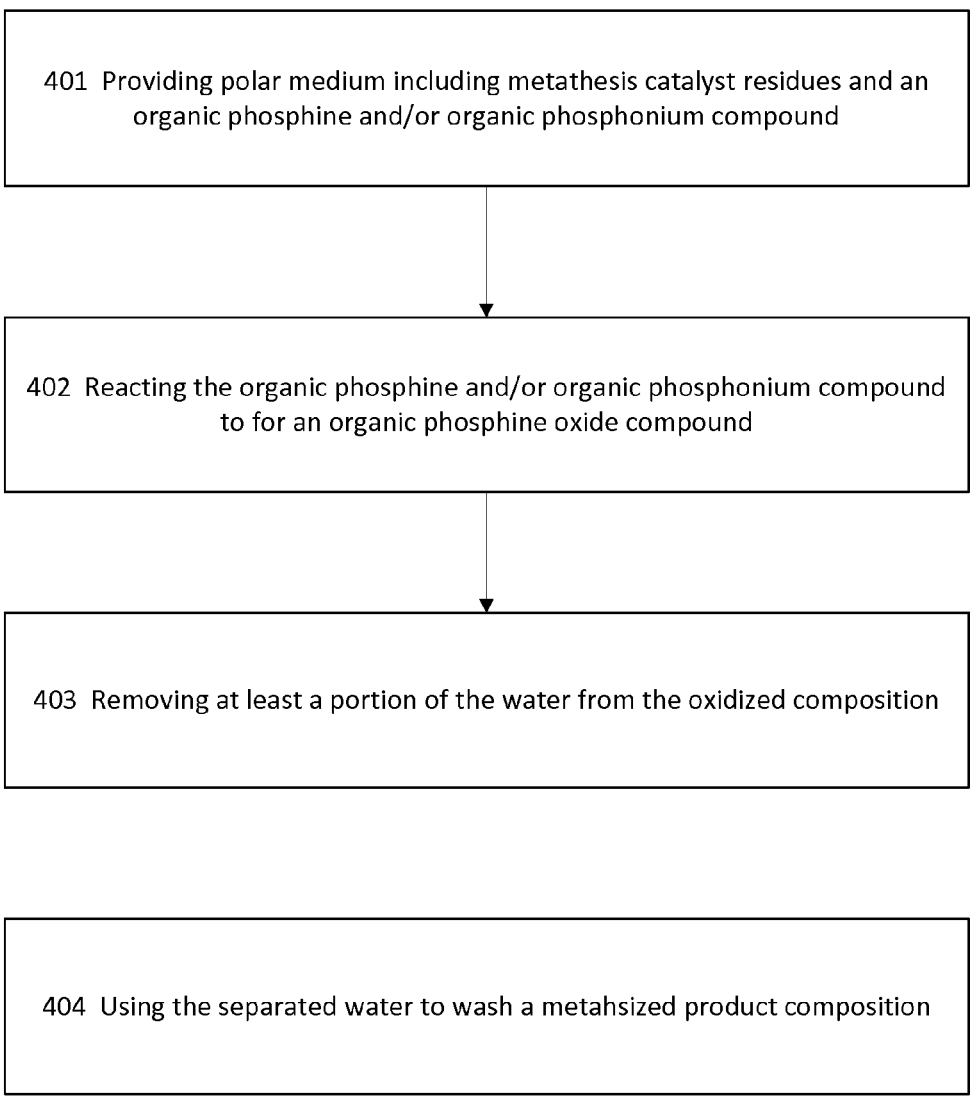
FIG. 4 shows an illustrative embodiment of treating a wastewater stream.

FIG. 4 illustrates some embodiments of the methods disclosed herein. In such embodiments, the methods 400 include: providing a polar (or aqueous) medium that contains metathesis catalyst residues and organic phosphine and/or organic phosphonium compounds 401; reacting the organic phosphine and/or organic phosphonium compounds in the polar medium to form organic phosphine oxide compounds 402; removing or separating at least a portion of the water from the oxidized composition (e.g., from the reacting 402) 403; and using the removed or separated water to wash a metathesized product composition (e.g., from a metathesis reactor) 404. Other optional steps can also be included. For example, in some embodiments, at least a portion of the catalyst residues are recovered from the polar medium after the providing 401 and before the reacting 402. In some other embodiments, at least a portion of the catalyst residues are recovered from the polar medium after the reacting 402, which may be done instead of an earlier catalyst residue recovery step or in combination with an earlier catalyst residue recovery step. Further, it should be noted that the reacting 402 can also include oxidizing other species in the polar medium that may be susceptible to oxidation. For example, in some embodiments, one or more aldehydes (e.g., formaldehyde) can be present in the polar medium, which are oxidized to alcohols (e.g., methanol) and acids (e.g., formic acid) in the reacting 402. Further, in some embodiments, one or more chemical treatments can be carried out after the reacting 402 and before the removing/separating 403. These can be carried out before, after, or concurrently with any catalyst recovery efforts. The chemical treatment can include various treatments or combinations of treatments, including, but not limited to, adjusting the pH (e.g., to be less alkaline), introducing various anions (e.g., sulfites), and introducing compounds to break down or assist in breaking down any residual peroxides.

Incorporation into Biorefinery Flow

The above-disclosed treatment methods can suitably be included into a biorefinery flow. This can be done in any suitable manner. In some embodiments, such methods include methods of refining a natural-oil-derived feedstock, which include: providing a feedstock comprising a natural oil or a derivative thereof; reacting the feedstock in the presence of a metathesis catalyst to form a metathesized product that comprises unsaturated esters and olefins; introducing an organic phosphine and/or phosphonium compounds to the metathesized product; washing the metathesized product with an aqueous wash solution to generate a washed metathesized product and a first aqueous medium comprising an organic phosphine and/or phosphonium compounds, and metathesis catalyst residues; separating at least a portion of the first aqueous medium from the washed metathesized product; and treating the separated first aqueous medium according to the method of any one of the above embodiments. Details regarding various steps of such methods are described in further detail above.

Figure 5:
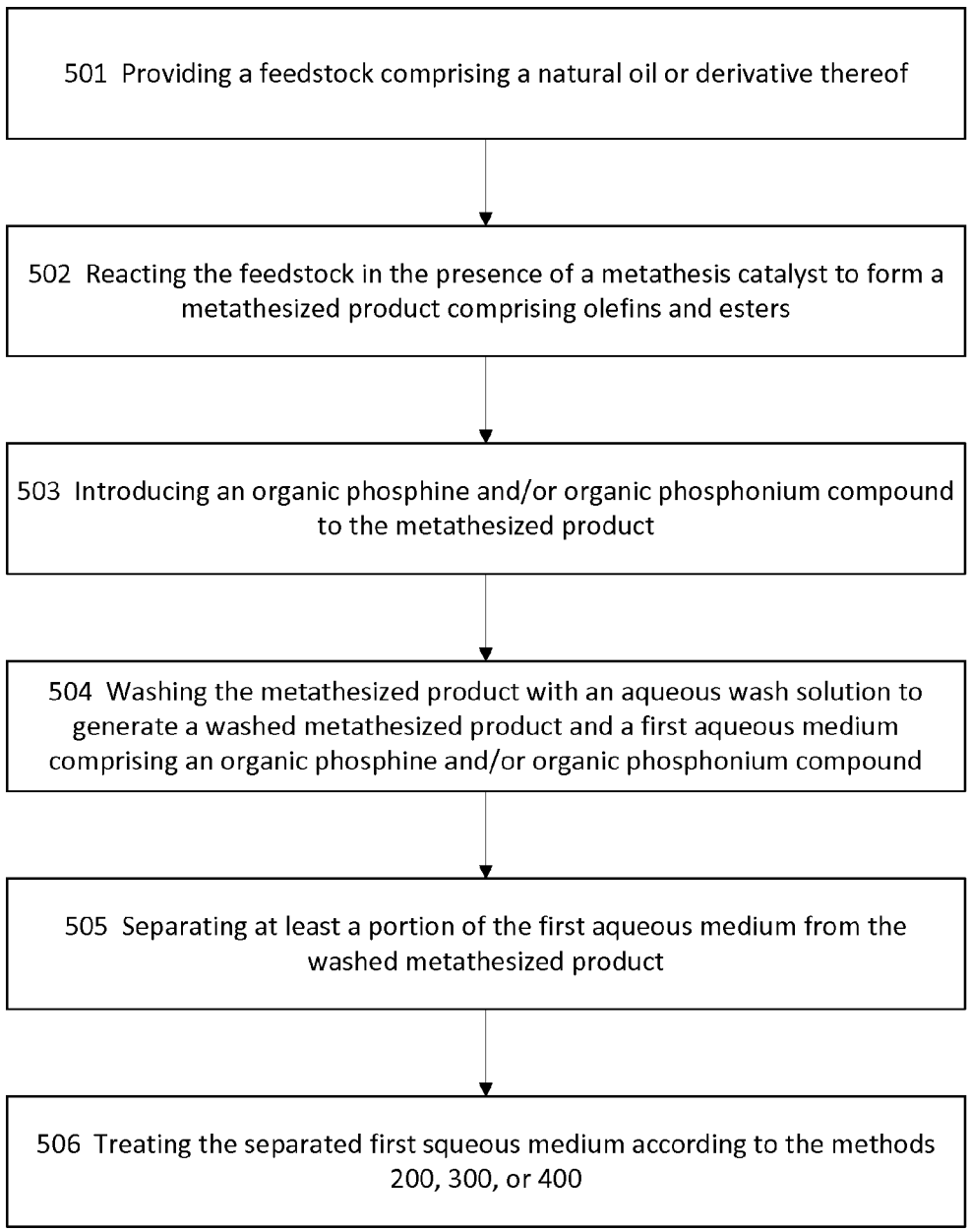
FIG. 5 shows an illustrative embodiment of treating a wastewater stream incorporated into a biorefinery process.

FIG. 5 illustrates some embodiments of the methods disclosed herein. In such embodiments, the methods 500 include: providing a feedstock comprising a natural oil or a derivative thereof 501; reacting the feedstock in the presence of a metathesis catalyst to form a metathesized product that comprises unsaturated esters and olefins 502; introducing an organic phosphine and/or phosphonium compounds to the metathesized product 503; washing the metathesized product with an aqueous wash solution to generate a washed metathesized product and a first aqueous medium comprising an organic phosphine and/or phosphonium compounds and metathesis catalyst residues 504; separating at least a portion of the first aqueous medium from the washed metathesized product 505; and treating the separated first aqueous medium 506 according to methods 200, 300, or 400.

Figure 6:
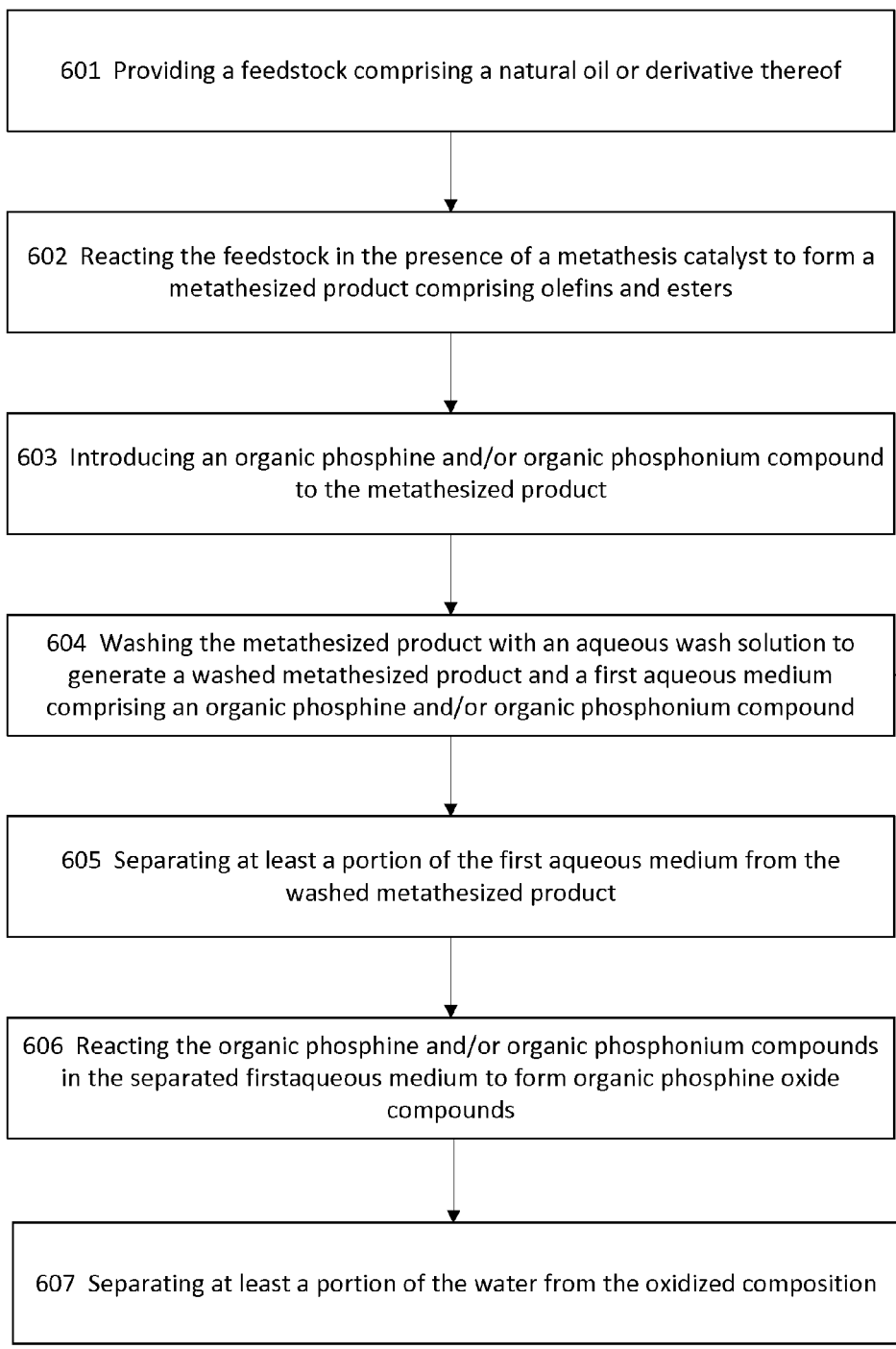
FIG. 6 shows an illustrative embodiment of treating a wastewater stream incorporated into a biorefinery process.

FIG. 6 illustrates some embodiments of the methods disclosed herein. In such embodiments, the methods 600 include: providing a feedstock comprising a natural oil or a derivative thereof 601; reacting the feedstock in the presence of a metathesis catalyst to form a metathesized product that comprises unsaturated esters and olefins 602; introducing an organic phosphine and/or phosphonium compounds to the metathesized product 603; washing the metathesized product with an aqueous wash solution to generate a washed metathesized product and a first aqueous medium comprising an organic phosphine and/or phosphonium compounds and metathesis catalyst residues 604; separating at least a portion of the first aqueous medium from the washed metathesized product 605; and reacting the organic phosphine and/or organic phosphonium compounds in the first aqueous medium to form organic phosphine oxide compounds 606; removing or separating at least a portion of the water from the oxidized composition (e.g., from the reacting 606) 607; and using the removed or separated water to wash a metathesized product composition 604. Other optional steps can also be included. For example, in some embodiments, at least a portion of the catalyst residues are recovered from the polar medium after the separating 605 and before the reacting 606. In some other embodiments, at least a portion of the catalyst residues are recovered from the polar medium after the reacting 606, which may be done instead of an earlier catalyst residue recovery step or in combination with an earlier catalyst residue recovery step. Further, it should be noted that the reacting 606 can also include oxidizing other species in the polar medium that may be susceptible to oxidation. For example, in some embodiments, one or more aldehydes (e.g., formaldehyde) can be present in the polar medium, which are oxidized to alcohols (e.g., methanol) and acids (e.g., formic acid) in the reacting 606. Further, in some embodiments, one or more chemical treatments can be carried out after the reacting 606 and before the removing/separating 607. These can be carried out before, after, or concurrently with any catalyst recovery efforts. The chemical treatment can include various treatments or combinations of treatments, including, but not limited to, adjusting the pH (e.g., to be less alkaline), introducing various anions (e.g., sulfites), and introducing compounds to break down or assist in breaking down any residual peroxides.

EXAMPLES

The following examples illustrate certain embodiments of the methods disclosed herein. The examples are provided for illustrative purposes only, and are not intended to limit the scope of the claimed subject matter.

Example 1

Collection of Wastewater Stream

A solution of 585 g toluene, 2.5 g 1-octene, and 3.8 g palm oil was heated to 60° C. and sparged with $N_2$. Then, 25 g of metathesis catalyst (C827, Materia, Inc., Pasadena, Calif.) was added to the solution and stirred for one hour at 60° C. A second flask containing 409 g tetrakis(hydroxymethyl)phosphonium sulfate (THPS, BRICORR 75, Solvay USA, Inc., Cranbury, N.J.) was treated with a mixture of 60.5 g 50% NaOH and 204.5 g water. The diluted THPS solution was added to the toluene solution and stirred while the temperature was increased to 90° C. and held for 1.5 hours. Stirring and heating were stopped, and the phases were allowed to separate. The aqueous layer was removed.

Example 2

Treatment of Aqueous Solution Containing Formaldehyde, THMP, and THPS

Approximately 50.45 g of a concentrated waste water stream, prepared according to Example 1, was diluted by the addition of 950.02 g of house-purified deionized water, followed by mixing. The diluted sample contained tris(hydroxymethyl)-phosphine (THMP), tetrakis(hydroxymethyl) phosphonium sulfate (THPS), sodium sulfate, tris(hydroxymethyl)phosphine oxide (THMPO), formaldehyde, and ruthenium containing organometallic species (e.g., metathesis catalyst residues). The presence of THMP, THPS, and THMPO were confirmed using $^{31}P$ NMR, while the presence of formaldehyde was confirmed using $^{13}C$ NMR. A 150.14 g sample of the diluted water stream was added to a 250 mL three-necked round-bottom flask equipped with a pH probe, temperature probe, condenser, slow $N_2$ headspace bleed, and a stir bar. The solution was heated in the flask to 32° C., followed by the addition of 1.5 mL of 50% (wt) NaOH in water. For the ensuing 2 hours, the temperature was maintained at 31 to 33° C. and the pH at 11.8 to 12.2. Samples were collected at regular intervals during the course of the 2-hour period.

Upon collection, each sample was neutralized using 85% (wt) phosphoric acid in water. The samples were analyzed for THMPO, THMP, THPS, formaldehyde, formic acid, and methanol using a combination of high performance liquid chromatography (HPLC) and NMR ($^{31}P$ and $^{13}C$). At the 2-hour point, the amount of THMP and THPS in the sample was determined to be below the detection limit (i.e., less than 100 ppm). Table 1 shows the recorded conditions at certain time intervals, as well as the measured concentration (in ppm) of THMPO, formaldehyde, methanol, and formic acid in the sample.

TABLE 1

|  | 1A | 1B | 1C | 1D | 1E | 1F |
| --- | --- | --- | --- | --- | --- | --- |
| Time (min) | 0* | 0 | 30 | 60 | 90 | 120 |
| Temp (° C.) | 31.1 | 32.8 | 32.3 | 31.6 | 32.2 | 31.7 |
| pH | 4.43 | 12.23 | 12.02 | 11.99 | 11.97 | 11.96 |
| THMPO (ppm) | 633.3 | 5238 | 8395 | 8430 | 8440 | 8444 |
| Formaldehyde (ppm) | 86.7 | 339 | 135.7 | 26.1 | 4.9 | 0.9 |

TABLE 1-continued

|  | 1A | 1B | 1C | 1D | 1E | 1F |
|---|---|---|---|---|---|---|
| Methanol (ppm) | 92.2 | 161.6 | 781.3 | 949.6 | 881.7 | 961.1 |
| Formic acid (ppm)** | 643 | 772 | 1654 | 1823 | 1900 | 1920 |

*Sample 1A was collected immediately before addition of the base.
**Measured as formate anion.

The results indicate near complete conversion of the phosphine and phosphonium compounds to phosphine oxide compounds within 2 hours, with the conversion more than 90% complete after only 1 hour.

Example 3

Treatment of Aqueous Solution Containing Formaldehyde, THMP, and THPS

Approximately 50.02 g of a concentrated waste water stream, prepared according to Example 3 (below), was diluted by the addition of 450.21 g of house-purified deionized water, followed by mixing. The diluted sample contained THMP, THPS, sodium sulfate, THMPO, formaldehyde, and ruthenium containing organometallic species (e.g., metathesis catalyst residues). The presence of THMP, THPS, and THMPO were confirmed using $^{31}$P NMR, while the presence of formaldehyde was confirmed using $^{13}$C NMR. The concentrations of these species were roughly 10 times their concentrations in Example 1. A 150.14 g sample of the diluted water stream was added to a 250 mL three-necked round-bottom flask equipped with a pH probe, temperature probe, condenser, slow N$_2$ headspace bleed, and a stir bar. The solution was heated in the flask to 32° C., followed by the addition of 1.5 mL of 50% (wt) NaOH in water. For the ensuing 6 hours, the temperature was maintained at 31 to 33° C. and the pH at 10 to 12. Samples were collected at regular intervals during the course of the 6-hour period.

Upon collection, each sample was neutralized using 85% (wt) phosphoric acid in water. The samples were analyzed for THMPO, THMP, THPS, formaldehyde, formic acid, and methanol using a combination of high performance liquid chromatography (HPLC) and NMR ($^{31}$P and $^{13}$C). At the 6-hour point, the amount of THMP and THPS in the sample was determined to be below the detection limit (i.e., less than 100 ppm). Table 2 shows the recorded conditions at certain time intervals, as well as the measured concentration (in ppm) of THMPO, formaldehyde, methanol, and formic acid in the sample.

TABLE 2

|  | 2A | 2B | 2C | 2D | 2E | 2F |
|---|---|---|---|---|---|---|
| Time (min) | 0 | 120 | 180 | 240 | 300 | 360 |
| pH | 4.83 | 11.21 | 11.10 | 11.02 | 10.97 | 11.96 |
| THMPO (ppm) |  | 16478 | 17312 | 18141 | 17502 | 17849 |
| Formaldehyde (ppm) |  | 354 | 213 | 162 | 122 | 77 |
| Methanol (ppm) |  | 1638 | 1616 | 1812 | 1935 | 1905 |
| Formic acid (ppm)* |  | 3190 | 3473 | 3580 | 3688 | 3727 |

*Measured as formate anion.

The results indicate near complete conversion of the phosphine and phosphonium compounds to phosphine oxide compounds within 6 hours.

Example 4

Biodegradability Determination

A 2.5 kg sample of the removed aqueous layer from Example 1 was heated to 50° C. and purged with N$_2$. The stirred solution was treated dropwise with 375.5 g 50% NaOH under a continuous N$_2$ purge. During the addition, vigorous gas evolution was observed. The base addition rate was monitored to dissipate gas and maintain a solution temperature of 50 to 60° C. Heating was discontinued and the solution was stirred overnight. Conversion of the starting materials was verified by NMR ($^{31}$P and $^{13}$C). The resulting solution was tested to determine its biological oxygen demand (BOD$_5$) using Standard Method No. 5210 B (United States Environmental Protection Agency, Arlington, Va., USA). The diluent solution contained methanol (150 ppm) and glycerine (150 ppm) in deionized water. The theoretical total BOD was determined to be 400 mg/L (COD), while the measured BOD was determined to be 282 mg/L. Thus, the BOD-to-COD ratio is 0.705, indicating that the treated sample is easily biodegradable (i.e., has a BOD-to-COD ratio >0.5).

What is claimed is:

1. A method of treating a reactor water stream, the method comprising:
    providing a first aqueous medium comprising (i) an organic phosphine compound or an organic phosphonium compound, and (ii) a metathesis catalyst residue; and
    reacting the organic phosphine compound or the organic phosphonium compound with an oxidizing agent to form a second aqueous medium comprising an organic phosphine oxide.

2. The method of claim 1, wherein the organic phosphine compound is a compound according to formula (Ia):

(Ia)

wherein R$^1$, R$^2$, and R$^3$ are independently a hydrogen atom or a C$_{1-20}$ hydrocarbyl group, wherein one or more of the carbon atoms in the hydrocarbyl group can be replaced by a heteroatom selected from the group consisting of nitrogen, oxygen, sulfur, and oxidized forms thereof;

wherein at least one of $R^1$, $R^2$, and $R^3$ is not a hydrogen atom.

3. The method of claim 2, wherein the organic phosphonium compound is a compound according to formula (Ib):

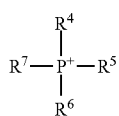

(Ib)

wherein $R^4$, $R^5$, $R^6$, and $R^7$ are independently a hydrogen atom or a $C_{1-20}$ hydrocarbyl group, wherein one or more of the carbon atoms in the hydrocarbyl group can be replaced by a heteroatom selected from the group consisting of nitrogen, oxygen, sulfur, and oxidized forms thereof;

wherein at least one of $R^4$, $R^5$, $R^6$, and $R^7$ is not a hydrogen atom.

4. The method of claim 1, wherein the first aqueous medium comprises the organic phosphonium compound and one or more counterions to the organic phosphonium compound.

5. The method of claim 4, wherein the one or more counterions are selected from the group consisting of: a halide anion, a sulfate anion, a hydrogen sulfate anion, a phosphate anion, a hydrogen phosphate anion, a dihydrogen phosphate anion, a nitrate anion, a hydroxide anion, a carbonate anion, a hydrogen carbonate anion, a cyanide anion, an acetate anion, a formate anion, an oxalate anion, and any mixtures thereof.

6. The method of claim 5, wherein the one or more counteranions are selected from the group consisting of: a chloride anion, a sulfate anion, and any mixtures thereof.

7. The method of claim 1, further comprising separating at least a portion of the metathesis catalyst residue from the first aqueous medium.

8. The method of claim 1, wherein the second aqueous medium comprises an amount of the metathesis catalyst residue.

9. The method of claim 8, further comprising separating at least a portion of the metathesis catalyst residue from the second aqueous medium.

10. The method of claim 1, wherein the first aqueous medium comprises an aldehyde, and wherein the method further comprises reacting the aldehyde with the oxidizing agent to form (i) an alcohol, and (ii) a carboxylic acid, a carboxylate, or a mixture thereof.

11. The method of claim 10, wherein the aldehyde is formaldehyde, the alcohol is methanol, the carboxylic acid is formic acid, and the carboxylate is formate.

12. The method of claim 1, wherein the oxidizing agent is an organic peroxide.

13. The method of claim 1, wherein the oxidizing agent is hydrogen peroxide, another inorganic peroxide, oxygen, ozone, a hypochlorite, a chlorate, nitric acid, chromium trioxide, a chromate, a dichromate, a manganite, or a permanganate.

14. The method of claim 1, wherein the reacting occurs in a basic medium.

15. The method of claim 14, wherein the pH of the basic medium is from 8 to 12.

16. The method of claim 1, further comprising chemically treating the second aqueous medium.

17. The method of claim 16, wherein the treating comprises introducing an acid to the second aqueous medium.

18. The method of claim 16, wherein the treating comprises introducing a sulfite to the second aqueous medium.

19. The method of claim 16, wherein the treating comprises introducing a peroxide decomposition catalyst to the second aqueous medium.

20. The method of claim 19, wherein the peroxide decomposition catalyst is a transition metal compound, such as palladium, platinum, silver, or manganese dioxide.

* * * * *